United States Patent
Cretin

(10) Patent No.: US 9,746,322 B2
(45) Date of Patent: Aug. 29, 2017

(54) THICKNESS MEASURING DEVICE AND THICKNESS MEASURING METHOD

(71) Applicant: Furuno Electric Co., Ltd., Nishinomiya (JP)

(72) Inventor: Dorian Cretin, Nishinomiya (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 351 days.

(21) Appl. No.: 14/426,944

(22) PCT Filed: Sep. 4, 2013

(86) PCT No.: PCT/JP2013/073754
§ 371 (c)(1),
(2) Date: Mar. 9, 2015

(87) PCT Pub. No.: WO2014/038569
PCT Pub. Date: Mar. 13, 2014

(65) Prior Publication Data
US 2015/0211844 A1 Jul. 30, 2015

(30) Foreign Application Priority Data
Sep. 10, 2012 (JP) .................. 2012-198835

(51) Int. Cl.
*G01B 21/20* (2006.01)
*G01B 17/02* (2006.01)
*A61B 8/08* (2006.01)

(52) U.S. Cl.
CPC ............ *G01B 17/02* (2013.01); *A61B 8/0858* (2013.01); *A61B 8/0875* (2013.01)

(58) Field of Classification Search
CPC .... A61B 8/0858; A61B 8/0875; G01B 17/02; G01N 29/348; G01N 29/46

(Continued)

(56) References Cited

U.S. PATENT DOCUMENTS

| | | | | |
|---|---|---|---|---|
| 6,494,097 B1 * | 12/2002 | Shihadeh | ............ | A61B 8/0858 600/438 |
| 8,679,019 B2 * | 3/2014 | Jurvelin | ............... | A61B 8/0858 600/438 |

(Continued)

FOREIGN PATENT DOCUMENTS

| | | |
|---|---|---|
| CN | 102469987 A | 5/2012 |
| JP | 200961079 A | 3/2009 |

(Continued)

OTHER PUBLICATIONS

Wear, K., "Autocorrelation and Cepstral Methods for Measurement of Tibial Cortical Thickness," IEEE Transactions on Ultrasonics, Ferroelectrics, and Frequency Control, vol. 50, No. 6, Jun. 2003, 6 pages.

(Continued)

*Primary Examiner* — An Do
(74) *Attorney, Agent, or Firm* — Alleman Hall Creasman & Tuttle LLP

(57) ABSTRACT

A thickness measuring device using ultrasonic waves is provided. A cortical bone thickness measuring device includes a plurality of oscillators, a reception waveform storage, an echo waveform synthesizing module, an inner-surface focusing waveform acquiring module, and a thickness calculating module. The plurality of oscillators are arrayed and each of the oscillators is transmittable and receivable of an ultrasonic wave. The echo waveform synthesizing module obtains an echo waveform corresponding to the ultrasonic beams by synthesizing reception waveforms of the respective oscillators stored in the reception waveform storage in advance, while scanning a focusing position of the ultrasonic beams. Concerning the obtained echo waveform, when it is determined that the beams suitably focus on an inner surface of a cortical bone as a result of an evaluation by the inner-surface focusing waveform acquiring module, the thickness calculating module calculates the thickness of the cortical bone based on the echo waveform.

20 Claims, 8 Drawing Sheets

(58) Field of Classification Search
USPC .......... 702/127, 155, 170, 171; 600/438; 73/602
See application file for complete search history.

(56) References Cited

U.S. PATENT DOCUMENTS

| | | |
|---|---|---|
| 2009/0069683 A1 | 3/2009 | Miyasaka |
| 2009/0112094 A1 | 4/2009 | Qin et al. |
| 2010/0018313 A1 | 1/2010 | Suetoshi et al. |
| 2012/0179042 A1 | 7/2012 | Fukumoto et al. |

FOREIGN PATENT DOCUMENTS

| | | |
|---|---|---|
| JP | 2009153945 A | 7/2009 |
| JP | 201029241 A | 2/2010 |
| JP | 4602972 B2 | 12/2010 |
| WO | 2007120890 A2 | 10/2007 |

OTHER PUBLICATIONS

Moilanen, P. et al., "Assessment of the Tibia Using Ultrasonic Guided Waves in Pubertal Girls," Osteoporosis International, vol. 14, No. 12, Dec. 2003, Available Online Oct. 2003, 8 pages.

Karjalainen, J. et al., "Ultrasonic Assessment of Cortical Bone Thickness In Vitro and In Vivo," IEEE Transactions on Ultrasonics, Ferroelectrics, and Frequency Control, vol. 55, No. 10, Oct. 2008, 7 pages.

Kilappa, V. et al., "Low-Frequency Axial Ultrasound Velocity Correlates With Bone Mineral Density and Cortical Thickness in the Radius and Tibia in Pre- and Postmenopausal Women," Osteoporosis International, vol. 22, No. 4, Apr. 2011, Available Online Jun. 2010, 11 pages.

ISA Japanese Patent Office, International Search Report Issued in Application No. PCT/JP2013/073754, Oct. 8, 2013, WIPO, 2 pages.

* cited by examiner

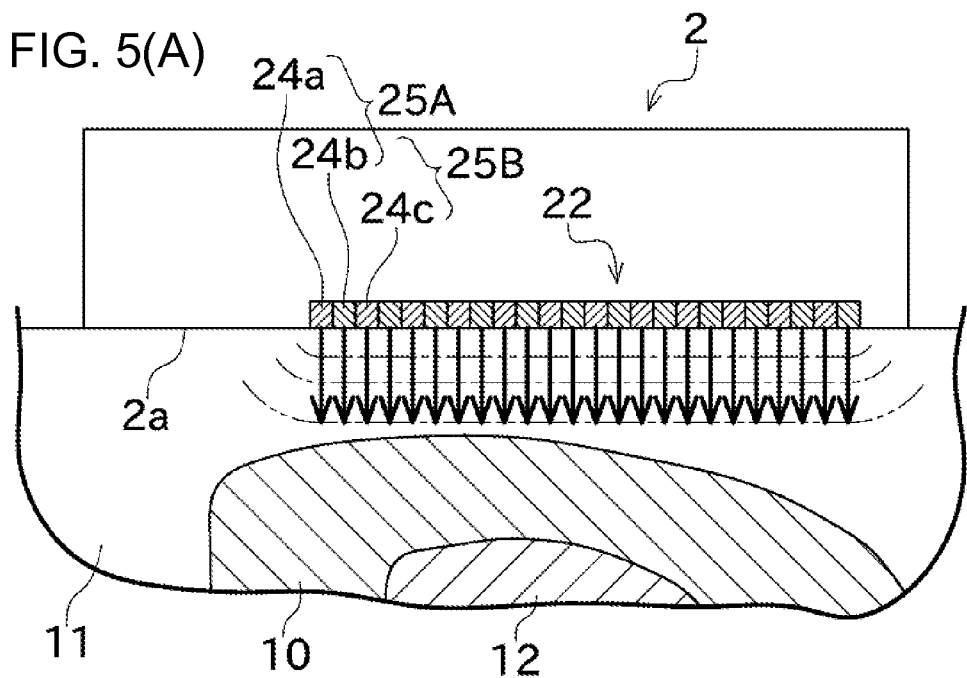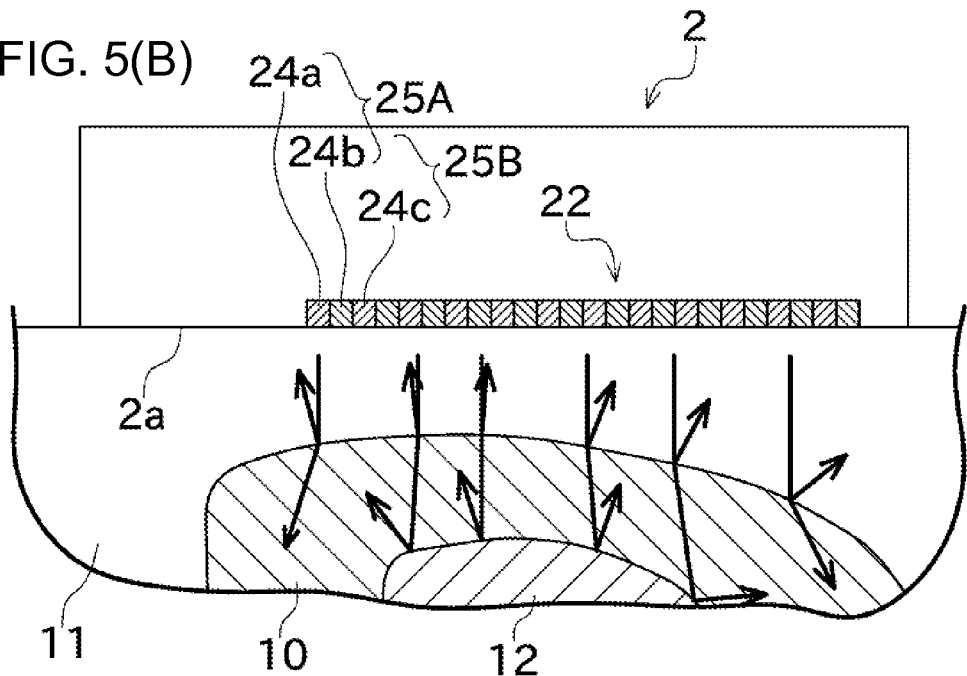

THICKNESS MEASURING DEVICE AND THICKNESS MEASURING METHOD

TECHNICAL FIELD

The present disclosure mainly relates to a thickness measuring device, which obtains echo signals by radiating ultrasonic waves to a target object, and measures a thickness of the target object based on the echo signals.

BACKGROUND ART

This kind of thickness measuring device is disclosed in, for example, Patent Document 1. The ultrasonic diagnosing device of Patent Document 1 is configured to perform a property diagnosis of blood vessel wall tissues. The ultrasonic diagnosing device is provided with an ultrasonic probe supported to closely contact with the body surface of an examinee. The ultrasonic probe includes a plurality of ultrasonic oscillators arranged in an array state. The ultrasonic diagnosing device transmits ultrasonic waves from the ultrasonic probe to the inside of body tissues of the examinee including the extravascular tissue and blood vessels. Then, some of ultrasonic waves reflected on the blood vessels, etc. and scattered, return to the ultrasonic probe and received as echoes. Here, by controlling a delay time length of a drive pulse signal supplied to the ultrasonic oscillator group, a direction and a focus depth of an acoustic ray of each ultrasonic beam transmitted from the ultrasonic probe are changed. Further, by controlling a delay time length of each of the reception signals of the respective ultrasonic oscillators, an opening diameter and a focus position of the ultrasonic probe can also be changed.

The ultrasonic diagnosing device of Patent Document 1 performs analysis and calculation of the reception echo signals and obtains elasticity of the extravascular tissue and the blood vessels. Note that, the ultrasonic diagnosing device of Patent Document 1 has a configuration basically of obtaining a change amount of a thickness between two positions, but it is also disclosed that the thickness between the two positions itself can also be obtained in a case where particular information, such as initial values of the two positions, is provided.

Patent Document 1 discloses the ultrasonic diagnosing device configured to mainly measure the blood vessel wall tissues, and as osteoporosis recently comes to draw much attention, it has been considered to measure a thickness of the cortical bone which is said to have a strong relationship with bone mass. For example, Non-patent Documents 1 and 2 disclose arts for deriving the thickness of the cortical bone by performing spectral processing on echoes from the outer and inner surfaces of the cortical bone. Further, in Non-patent Documents 3 and 4, methods of calculating to obtain the thickness of the cortical bone by using low-frequency lamb waves are proposed.

REFERENCE DOCUMENTS OF CONVENTIONAL ART

Patent Document(s)

Patent Document 1: JP4602972B

Non-Patent Document(s)

Non-patent Document 1: Autocorrelation and Cepstral Methods for Measurement of Tibial Cortical Thickness, Wear et al., IEEE UFFC, vol 50. No. 6, June 2003

Non-patent Document 2: Ultrasonic Assessment of Cortical Bone Thickness In vitro and In vivo, J. Karjalainen et al., IEEE UFFC, vol 55. No. 10, October 2008

Non-patent Document 3: Assessment of the tibia using ultrasonic guided waves in pubertal girls, Moilanen et al., Osteoporosis International, vol. 14, 2003

Non-patent Document 4: Low-frequency axial ultrasound velocity correlates with bone mineral density and cortical thickness in the radius and tibia in pre- and postmenopausal women, Vilappa et al., vol 22, No. 4, 2011

DISCLOSURE

Problems to be Solved

However, the cortical bone described above, although there is an individual difference, has a feature that many cavities exist thereinside. Further, when using ultrasonic waves, the size of each cavity and the wavelength order substantially match. Therefore, in such a case where a cortical bone is the target object, if a thickness of the cortical bone is simply obtained by transceiving the ultrasonic beams as Patent Document 1, the echo signals from the inner surface of the cortical bone become hard to be acquired due to influence of scattering or the like caused by the cavities, and thus, it becomes difficult to measure the thickness at high accuracy.

Further, in a case where the thickness of the cortical bone is measured in the methods of Non-patent Documents 1 and 2, it is a prerequisite that ideal conditions are satisfied, such as the outer surface of the cortical bone is in parallel to the inner surface, the outer surface is flat, and the inside of bone is homogeneous. Therefore, there is no denying that it is difficult to ensure accuracy of the thickness measurement at a practical level for the actual cortical bone having many cavities and a curved shape.

On the other hand, as Non-patent Documents 3 and 4, in a case where the lamb waves are used, it is said that the thickness measurement accuracy has a limit due to the low frequency. Further, since a long propagation distance is needed when the lamb waves are used, there has been room for improvement also in view of robustness measurement.

The present disclosure is made in view of above situations and aims to provide a thickness measuring device, which is able to measuring a thickness of a target object at suitable accuracy by using ultrasonic waves even in an environment where many cavities exist between an outer surface and an inner surface of the target object or many unnecessary echoes are obtained.

SUMMARY

Problems to be solved by the present disclosure are described above, and means for solving the problems and effects thereof will be described below.

According to a first aspect of this disclosure, a thickness measuring device having the following configuration is provided. Specifically, the thickness measuring device includes a plurality of transducing parts, a reception waveform storage, an echo waveform synthesizing module, an inner-surface focusing waveform acquiring module, and a thickness calculating module. The plurality of transducing parts are arranged in line, each of the transducing parts being configured to be transmittable of an ultrasonic wave to a target object and acquirable of an echo signal with respect to the ultrasonic wave. The reception waveform storage acquires and stores reception waveforms of all of the transducing parts every time the respective transducing parts transmit the ultrasonic waves. The echo waveform synthesizing module obtains echo waveforms corresponding to the ultrasonic beams while scanning a focusing position of the ultrasonic beams, each of the echo waveforms being obtained by synthesizing the reception waveforms of the respective transducing parts stored in the reception waveform storage. The inner-surface focusing waveform acquiring module acquires the echo waveform in which the beams are suitably focused on an inner surface of the target object, by evaluating each of the echo waveforms obtained by the echo waveform synthesizing module. The thickness calculating module calculates a thickness of the target object based on the echo waveform acquired by the inner-surface focusing waveform acquiring module.

Thus, even in an environment where many cavities exist between an outer surface and the inner surface of the target object or many unnecessary echoes are obtained, the thickness of the target object can be measured at suitable accuracy by using the ultrasonic waves.

The thickness measuring device preferably has the following configuration. Specifically, the thickness measuring device includes an outer-surface detecting module configured to detect a position and shape of an outer surface of the target object. The echo waveform synthesizing module, upon acquiring or hypothetically determining speeds of sound inside and outside the target object, calculates a path of the ultrasonic wave arriving at the transducing part used on the reception side from the transducing part used on the transmission side via the focusing position by taking into consideration refraction of the path at the outer surface of the target object acquired by the outer-surface detecting module, and the echo waveform synthesizing module acquires the echo waveforms by synthesizing the reception waveforms based on the calculation result while scanning the focusing position.

Thus, each echo waveform can be synthesized while accurately simulating the propagation path of the ultrasonic wave. Therefore the accuracy of the thickness measurement can be improved.

With the thickness measuring device, the echo waveform synthesizing module preferably calculates a propagation time length of the ultrasonic wave arriving at the transducing part used on the reception side from the transducing part used on the transmission side via the focusing position, and the echo waveform synthesizing module preferably acquires the echo waveforms by synthesizing the reception waveforms while scanning the focusing position, each of the reception waveforms being synthesized while being shifted by a delay time length calculated based on the propagation time length.

Thus, the echo waveform in which the beams are suitably focused on the inner surface of the target object can be acquired through the scanning of the focusing position while synthesizing the echo waveforms based on the accurate calculation.

With the thickness measuring device, the echo waveform synthesizing module preferably scans the focusing position of the ultrasonic beams two-dimensionally.

Thus, the focusing position can be scanned in a large area inside the target object, which increases the possibility of obtaining the waveform in which the beams are suitably focused on the inner surface of the target object. Therefore, the accuracy of the thickness measurement can be improved.

With the thickness measuring device, the inner-surface focusing waveform acquiring module preferably acquires the echo waveform in which the beams are suitably focused on the inner surface of the target object, by forming each of the synthesized echo waveforms into an envelope and evaluates a shape of an echo pattern obtained from the envelope.

Thus, the echo waveform can be evaluated based on the shape of the envelope. Therefore, the echo waveform in which the beams are suitably focused on the inner surface of the target object can easily and surely be discriminated.

With the thickness measuring device, the thickness calculating module preferably calculates the thickness of the target object based on a time difference between an outer surface echo and an inner surface echo that appear in the echo waveform acquired by the inner-surface focusing waveform acquiring module.

Thus, the thickness of the target object can be obtained by the simple processing.

With the thickness measuring device, an array oscillator set provided with oscillators arranged in line are preferably provided, the oscillators being the plurality of transducing parts.

Thus, the simple arrangement of the transducing parts are achieved. Therefore, the echo waveform can accurately be synthesized from the reception waveforms stored in the reception waveform storage.

With the thickness measuring device, the plurality of oscillators provided in the array oscillator set are preferably transmittable of ultrasonic waves simultaneously and also transmittable of the ultrasonic waves at individual timings.

Thus, the reception waveform can be easily obtained by the oscillators transmitting the ultrasonic waves individually, and the plane wave obtained by the plurality of oscillators simultaneously transmitting the ultrasonic waves can be utilized in various occasions.

With the thickness measuring device, the target object is preferably a cortical bone.

Thus, the thickness of the cortical bone which is so said to have a strong relationship with the bone mass can be measured at high accuracy. Therefore, useful information can be provided in diagnosing a bone strength, etc.

According to a second aspect of this disclosure, the following method of measuring a thickness of a target object by a thickness measuring device including a plurality of transducing parts arranged in line, each of the transducing parts being configured to be transmittable of an ultrasonic wave to the target object and acquirable of an echo signal with respect to the ultrasonic wave is provided. The method includes acquiring and storing reception waveforms of all of the transducing parts every time each transducing part transmits the ultrasonic wave. The method includes obtaining echo waveforms corresponding to the ultrasonic beams while scanning a focusing position of the ultrasonic beams, each of the echo waveforms being obtained by synthesizing the reception waveforms of the respective transducing parts stored by the acquiring and storing the reception waveforms. The method includes acquiring the echo waveform in which the beams are suitably focused on an inner surface of the target object, by evaluating each of the echo waveforms obtained by the obtaining the echo waveforms. The method includes calculating a thickness of the target object based on the echo waveform acquired by the acquiring the echo waveform.

Thus, even in an environment where many cavities exist between an outer surface and the inner surface of the target object or many unnecessary echoes are obtained, the thickness of the target object can be measured at suitable accuracy by using the ultrasonic waves.

BRIEF DESCRIPTION OF DRAWINGS

FIG. 5(A) is a view illustrating a situation where a plane wave is transmitted by an array oscillator set, and FIG. 5(B) is a view illustrating a situation where the plane wave transmitted from the array oscillator set reflects on either one of an outer surface and the inner surface of the cortical bone.

EMBODIMENTS

Figure 1:
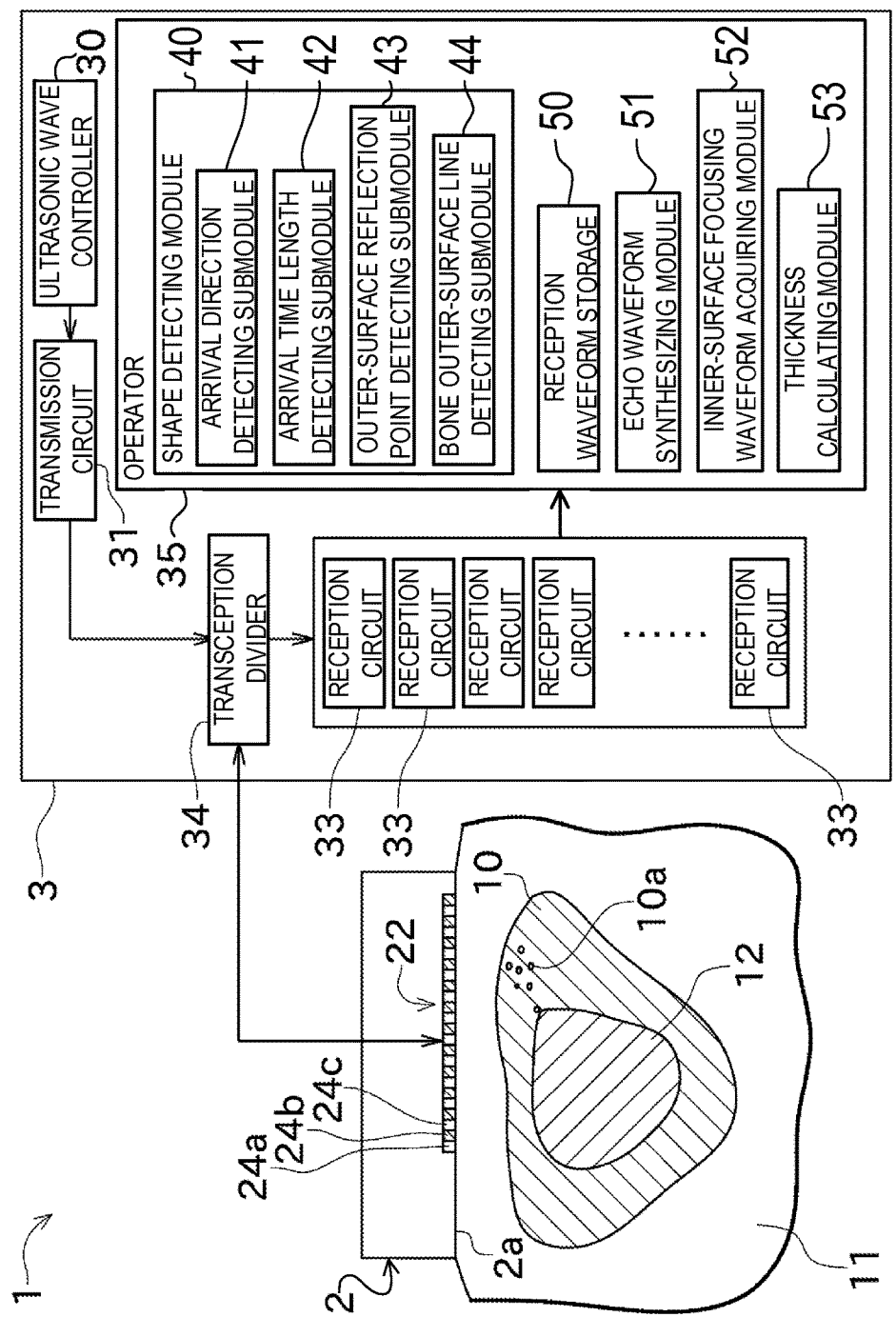
FIG. 1 shows a schematic cross-sectional view and a schematic functional block diagram of a cortical bone thickness measuring device according to one embodiment of this disclosure.

Next, one embodiment of this disclosure is described with reference to the drawings. FIG. 1 shows a schematic cross-sectional view and a schematic functional block diagram of a cortical bone thickness measuring device 1 according to the embodiment of this disclosure.

The cortical bone thickness measuring device (thickness measuring device) 1 diagnoses a strength of a cortical bone of a long tubular bone, such as a tibia (note that, the diagnosing target is not limited to this). To explain in detail, a bone generally includes a cortical bone 10 and a mesh-shaped cancellous bone 12 existing on the inner side of the cortical bone 10. Moreover, the cortical bone 10 is covered in its surrounding by a soft tissue 11, such as muscle or fat. The cortical bone measuring device of this embodiment is configured to radiate ultrasonic waves to the cortical bone 10 from outside of the soft tissue 11, and measure the thickness of the cortical bone 10. Therefore, in this embodiment, the cortical bone 10 corresponds to a target object.

The left part of FIG. 1 illustrates a cross section of a tibia part of a human body, taken by cutting the tibia part in a plane face orthogonal to a longitudinal direction of the bone. As illustrated in FIG. 1, a contour shape of an outer surface of the cortical bone 10 is formed by gentle curvy lines bulging in radial directions of the cortical bone 10 (directions orthogonal to the longitudinal direction of the bone). Thus, in the following description, by using the long tubular bone as a circular cylinder, the direction to which the ultrasonic waves propagate along the outer surface of the cortical bone 10 within the cross section may be referred to as the circumferential direction. On the other hand, although the illustration is omitted, in a cross section of the tibia part taken by cutting the tibia part in a plane face parallel to the longitudinal direction of the bone, the outer surface contour of the cortical bone 10 is formed by substantially straight lines.

Hereinafter, the configuration of the cortical bone thickness measuring device 1 is described in detail. As illustrated in FIG. 1, the cortical bone thickness measuring device 1 includes an ultrasonic wave transducer 2 and a device body 3.

The ultrasonic wave transducer 2 transmits and receives ultrasonic waves. The ultrasonic wave transducer 2 includes a contact face 2a contacting with an outer surface of the soft tissue 11 of the measurement position, and an array oscillator set 22. The array oscillator set 22 is comprised of a plurality of oscillators 24 arrayed in a line. Note that, as each of the oscillators used in this embodiment, an oscillator of which outer surface vibrates in response to a reception of an electric signal and radiates an ultrasonic wave, and which also generates and outputs an electric signal in response to a reception of an ultrasonic wave on the outer surface is adopted.

The array oscillator set 22 includes the plurality of oscillators (transducing parts) 24. Note that, in the following description, when the plurality of oscillators 24 need to be differentiated from each other, a small-letter alphabet is sequentially added to the end of each reference numeral from one side of the array oscillator set 22, so that they are expressed as the oscillator 24a, the oscillator 24b, the oscillator 24c, and so on. Moreover, similarly, for the purpose of specifying the individual oscillators 24, each of the plurality of oscillators 24 may be referred to by using the number of the oscillator 24 from one end of the array, for example, the oscillator 24a is the first, the oscillator 24b is the second, and so on. The oscillators 24 are arranged in a line at even intervals so as to be in parallel to the contact face 2a. Further, each oscillator 24 is configured to be able to transmit and receive the ultrasonic wave.

In actually transceiving the ultrasonic waves by using the ultrasonic wave transducer 2, an ultrasonic jelly is applied on a skin outer surface of the measurement position (i.e., outer surface of the soft tissue 11), and the contact face 2a is brought in contact with the skin outer surface. Then, the ultrasonic waves are transmitted from the array oscillator set 22. Thus, the ultrasonic waves contact to the cortical bone 10 as the target object, via the soft tissue 11. Further, the ultrasonic waves returning from the cortical bone 10 are received by the array oscillator set 22. Note that, the ultrasonic jelly prevents a gap from being formed between the soft tissue 11 and the contact face 2a and also matches acoustic impedances of the contact face 2a and the soft tissue 11 therebetween to reduce reflection of the ultrasonic waves, which are transmitted from the array oscillator set 22, on the outer surface of the soft tissue 11.

Next, the device body 3 is described. The device body 3 is connected to the ultrasonic wave transducer 2 via a cable and configured to be able to perform signal transception with the ultrasonic wave transducer 2. Specifically, the device body 3 includes an ultrasonic wave controller 30, a transmission circuit 31, a plurality of reception circuits 33, a transception divider 34, and an operator 35.

The transmission circuit 31 is configured to vibrate the array oscillator set 22 to cause the ultrasonic waves, by generating electric pulse signal(s) and transmitting it to the array oscillator set 22. A central frequency of the electric pulse vibration is about 1 to 10 MHz, for example. Note that, for example, a chirp signal may be used instead of the electric pulse signal.

Note that, the transmission circuit 31 is configured such that in causing the ultrasonic waves by the array oscillator set 22, it can generate the electric pulse signal at any timing for each of the plurality of oscillators 24. Moreover, the ultrasonic wave controller 30 is connected with the transmission circuit 31 and is configured to transmit to the transmission circuit 31 a control signal for transmitting the ultrasonic waves from the plurality of oscillators 24. Thus, a control can be performed to transmit the ultrasonic waves from the plurality of oscillators 24 at the same time or individual timings.

The plurality of reception circuits 33 are respectively connected, in correspondence with each other, with the plurality of oscillators 24 configuring the array oscillator set 22. Each of the reception circuits 33 is configured to receive the electric signal outputted from the single oscillator 24 in response to receiving the ultrasonic wave, perform amplification, filtering, digital conversion and the like on the electric signal to create a digital signal, and transmit it to the operator 35. Note that, the signals outputted directly from the array oscillator set 22 are analog waveform signals, and the signals transmitted to the operator 35 are signal-processed digital waveform signals; however, in the following description, each of the signals may simply be referred to as the "waveform signal" without differentiating them.

The transception divider 34 is connected between the array oscillator set 22, the transmission circuit 31, and the reception circuit 33. The transception divider 34 prevents the electric signal (electric pulse signal) to be transmitted from the transmission circuit 31 to the array oscillator set 22 from flowing directly to the reception circuits 33, and prevents the electric signal, which is to be transmitted from the array oscillator set 22 to the reception circuits 33, from flowing to the transmission circuit 31 side.

Next, a basic concept of a thickness measuring method of this embodiment is described with reference to FIGS. 2 and 3.

As the target for the ultrasonic waves to reflect on, other than the inner surface of the cortical bone 10 as described above, a cavity 10a can also be considered. However, the inner surface of the cortical bone 10 has different properties from those of the cavity 10a.

Specifically, the cavity 10a is comparatively small in size, includes a large number of cavities, and the locations thereof in the bone are irregular. Therefore, phases of reflection waves from the respective cavities 10a can be considered to appear randomly. On the other hand, the inner surface of the cortical bone 10 normally exists as a single large continuous surface. Therefore, phases of reflection waves from the inner surface of the cortical bone 10 can be considered to be close to each other.

Figure 2A:
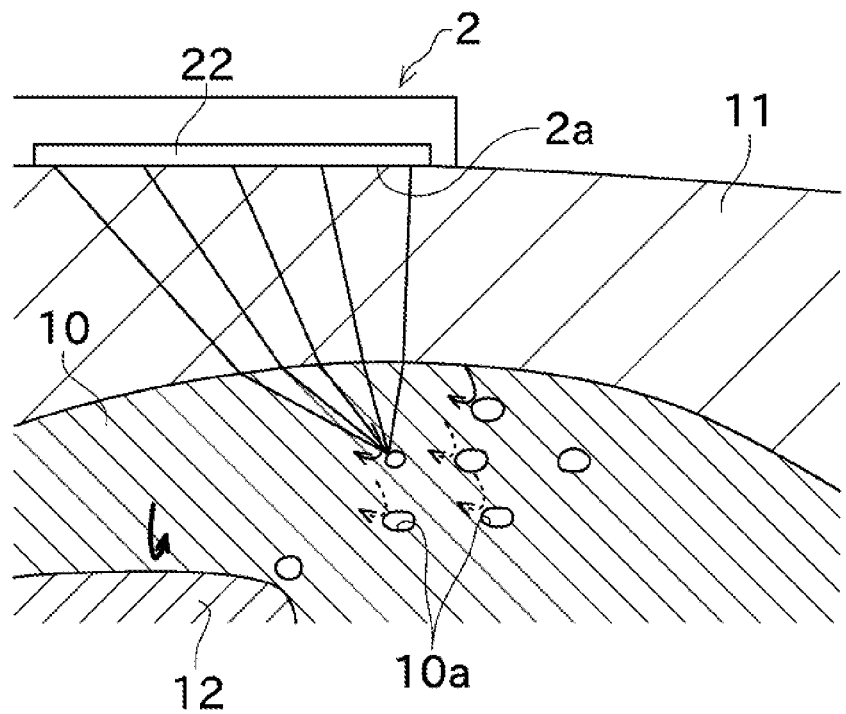
FIG. 2(A) is a conceptual view illustrating a situation where ultrasonic beams are focused on a cavity inside a cortical bone.
Figure 2B:
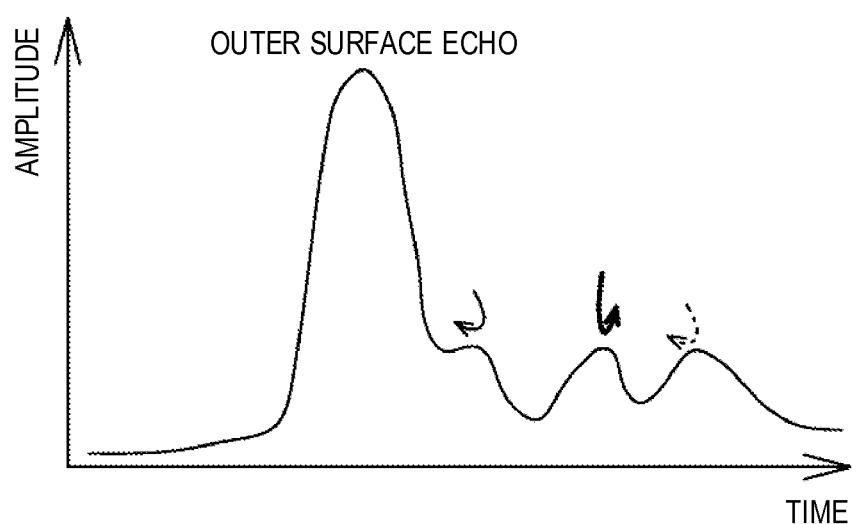
FIG. 2(B) is a chart illustrating an envelope of a reception waveform when focusing on the cavity.

Therefore, in a case where the ultrasonic beams are focused on one of the cavities 10a as illustrated in FIG. 2(A), the ultrasonic waves also reflect on the cavities 10a at different positions. Thus, echoes having various phases are received and weaken each other (destructive interference). Therefore, as illustrated in FIG. 2(B), in an envelope (echo pattern) of a reception waveform of this case, a peak does not explicitly appear other than at the outer surface of the cortical bone 10.

Figure 3A:
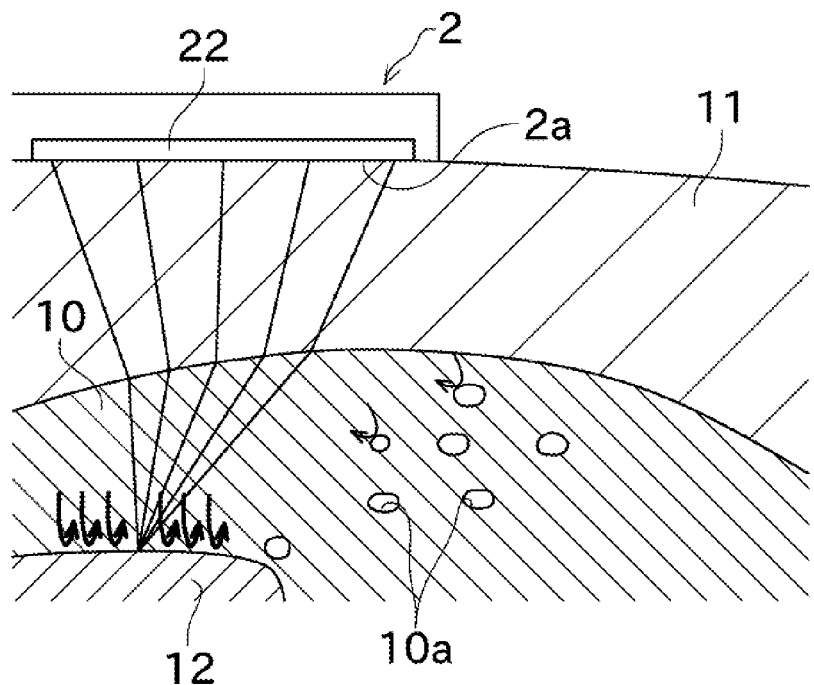
FIG. 3(A) is a conceptual view illustrating a situation where ultrasonic beams are focused on an inner surface of the cortical bone.
Figure 3B:
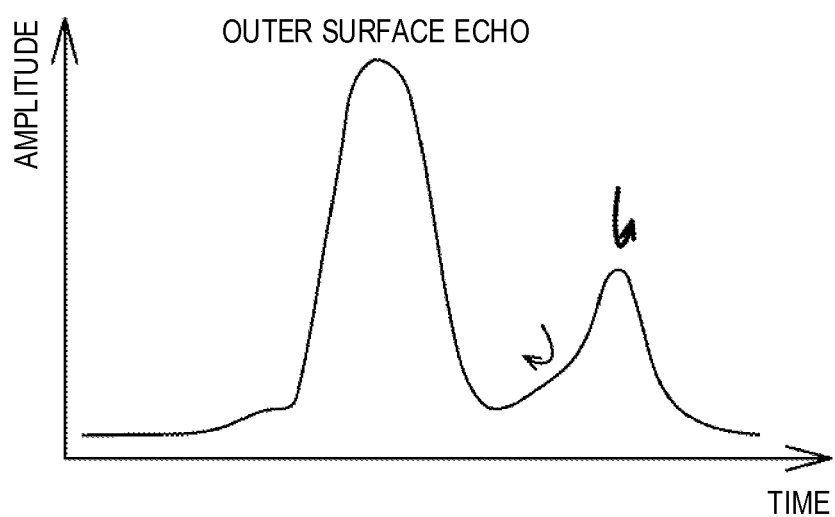
FIG. 3(B) is a chart illustrating an envelope of a reception waveform when focusing on the inner surface of the cortical bone.

On the other hand, when the ultrasonic beams are focused on the inner surface of the cortical bone 10 as illustrated FIG. 3(A), the echoes from the respective parts of the inner surface have the same phase, and therefore, they should strengthen each other (incremental interference). Therefore, as illustrated in FIG. 3(B), in an envelope (echo pattern) of a reception waveforms of this case, in addition to the peak of the reflection waves from the outer surface of the cortical bone 10, a peak of the reflection waves from the inner surface explicitly appears.

Therefore, by using the beam focusing method, the echoes from the inner surface of the cortical bone 10 can be considered to be effectively separated utilizing the difference in the properties described above, without letting it be hidden among unnecessary echoes.

However, since the location of the inner surface of the cortical bone 10 is not always certain, the inner surface cannot be instantly focused. Therefore, in this embodiment, the focusing position where the phases of the reflection waves from the inner surface of the cortical bone 10 match (focusing position which causes results as FIG. 3(A) and FIG. 3(B)) is searched for while suitably scanning the focusing position. Thus, the reception waveform (echo pattern) in which the echoes from the inner surface of the cortical bone 10 are suitably separated can securely be acquired.

Note that, due to the scanning of the focusing position, the peak of the reflection waves from the outer surface of the cortical bone 10 also changes. However, a speed of sound is slower in the soft tissue than in the cortical bone, and thus, when the focusing position is changed, the path of each ultrasonic wave changes less in the soft tissue than in the cortical bone. Therefore, even if the focusing position is changed, since the variation of the peak position caused by the reflection waves from the outer surface of the cortical bone 10 can be considered small, substantive influence on the thickness detection accuracy of the cortical bone 10 can be said to be small.

Figure 4:
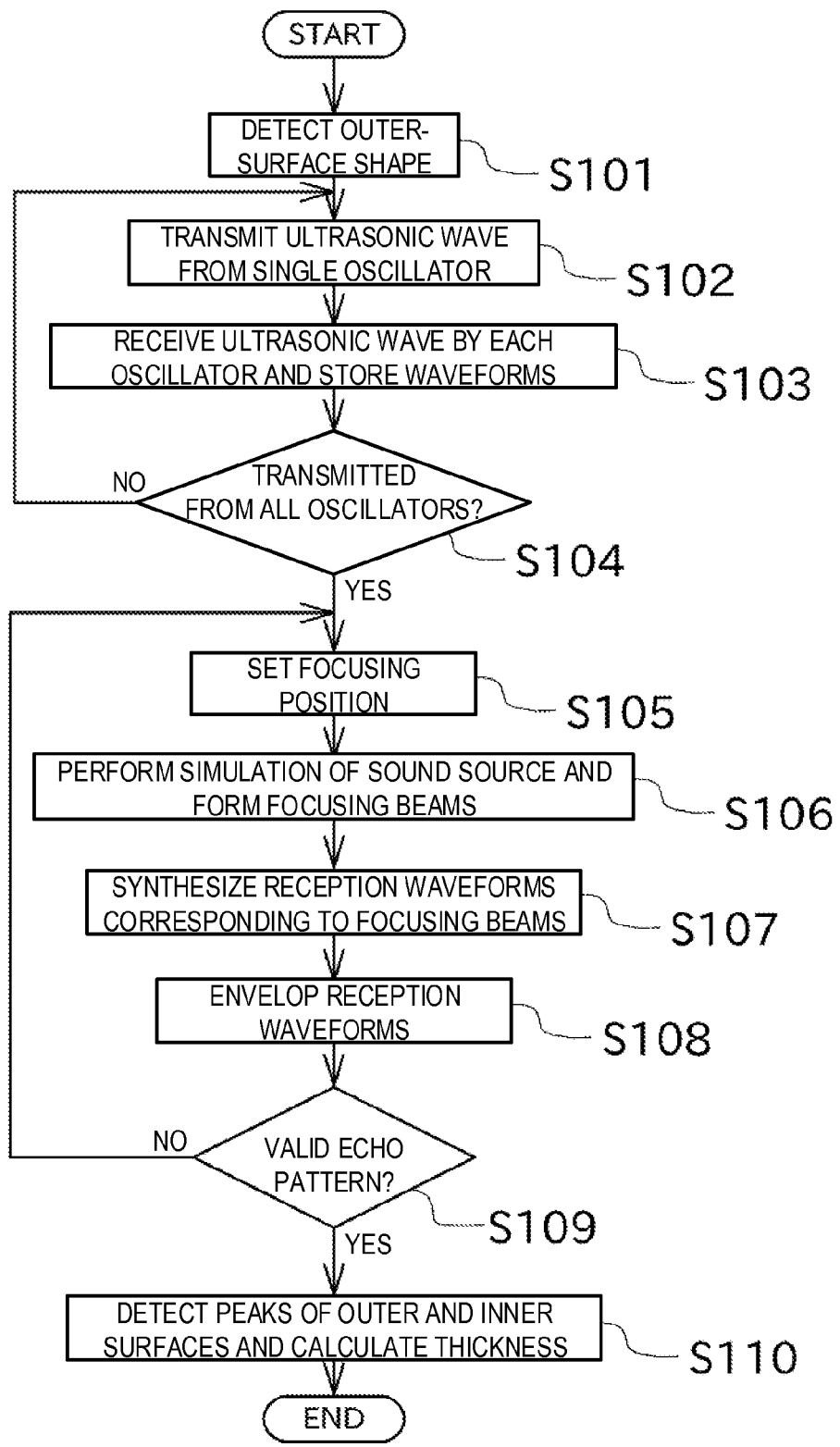
FIG. 4 is a flowchart of a thickness measuring method of this embodiment.

Next, a specific configuration for measuring the thickness of the cortical bone 10 by the cortical bone thickness measuring device 1 of this embodiment and processing performed by the cortical bone thickness measuring device 1 are described. FIG. 4 is a flowchart of the thickness measuring method of this embodiment.

The operator 35 provided to the device body 3 of the cortical bone thickness measuring device 1 illustrated in FIG. 1 is comprised of hardware, such as a CPU, a RAM and a ROM, and software, such as programs stored in the ROM and the like. Further, the operator 35 is configured such that the hardware cooperates with the software to function as a shape detecting module 40, a reception waveform storage 50, an echo waveform synthesizing module 51, an inner-surface focusing waveform acquiring module 52, a thickness calculating module 53 and the like. In other words, with the cortical bone thickness measuring device 1, the operator 35 measures the thickness of the cortical bone 10 by performing in series, shape detecting process, reception waveform storing process, echo waveform synthesizing process, inner-surface focusing waveform acquiring process, and thickness calculating process.

The shape detecting module 40 is described. The shape detecting module 40 performs detection of the bone outer surface shape beforehand so that an ultrasonic wave propagation path can be calculated in later-performed focusing beam forming. The function of the shape detecting module 40 corresponds to the processing at S101 (shape detection) in the flowchart of the FIG. 4.

Specifically, the shape of the outer surface of the cortical bone 10 (cross-sectional contour shape of the cortical bone 10) needs to be acquired in some way in order to obtain the propagation path of each ultrasonic wave. Thus, in this embodiment, the outer surface shape of the cortical bone 10 is detected by the shape detecting module 40 before the thickness calculating module 53 obtains the thickness of the cortical bone 10. Note that, although the outer surface shape of the cortical bone 10 may be measured by a different device using X-rays, etc., in this embodiment, the cortical bone thickness measuring device 1 measures the outer surface shape of the cortical bone 10 by using the ultrasonic waves. Thus, the ease of the measurement is improved.

In detecting the bone outer surface shape by the shape detecting module 40, the transmission of the ultrasonic waves from the array oscillator set 22 is performed as advance preparation. The situation where the ultrasonic waves are transmitted from the array oscillator set 22 is described with reference to FIGS. 5(A)-5(B). FIG. 5(A) is a view illustrating the situation where the ultrasonic waves are transmitted by the array oscillator set 22, and FIG. 5(B) is a view illustrating a situation where the ultrasonic waves transmitted from the array oscillator set 22 reflect on either one of the outer surface and the inner surface of the cortical bone 10.

In the case of transmitting the ultrasonic waves by the array oscillator set 22, the pulse signal from the transmission circuit 31 is sent to the array oscillator set 22, and the plurality of oscillators 24 configuring the array oscillator set 22 simultaneously transmit to the bone the ultrasonic waves in the same phase.

By simultaneously transmitting the ultrasonic waves from the plurality of oscillators 24, a plane wave as illustrated in FIG. 5(A) can be produced. The plane wave is in parallel to the contact face 2a and moves inside the soft tissue 11 in a direction orthogonal to the contact face 2a. The plane wave reflects on the outer and inner surfaces of the cortical bone 10 as FIG. 5(B), and is received by the oscillators 24.

Once the oscillators 24 receive the ultrasonic waves, the waveform signals corresponding to the ultrasonic waves received by the oscillators 24 are transmitted to the operator 35. By analyzing this waveform signals, the outer surface shape of the cortical bone 10 can be obtained.

Note that, theoretically, not only the ultrasonic waves reflected on the outer surface of the cortical bone 10, but also the ultrasonic waves reflected on the inner surface thereof are received by the oscillators 24. In the case where the plane wave is simply produced as FIG. 5(A), due to influence of the cavities 10a and the like, the reflection waves from the inner surface are difficult to capture in many cases compared to the reflection waves from the outer surface. Therefore, the echoes from the inner surface are not particularly analyzed by the shape detecting module 40 of this embodiment.

Hereinafter, the shape detecting module 40 is described in detail. The operator 35 functions as the shape detecting module 40 to detect an angle with respect to the oscillator 24 and a timing when each reflection wave is received by the corresponding oscillator 24, and the outer surface shape of the cortical bone 10 is obtained based on the angle and timing.

Specifically, the shape detecting module 40 includes an arrival direction detecting submodule 41, an arrival time length detecting submodule 42, an outer-surface reflection point detecting submodule 43, and a bone outer-surface line detecting submodule 44.

First, the arrival direction detecting submodule 41 is described. The arrival direction detecting submodule 41 determines oscillator pairs 25 by selecting two adjacent oscillators among the plurality of oscillators 24 as a single pair, and detects arrival directions of the ultrasonic waves reaching each oscillator pair 25. Note that, in the following description regarding the shape detecting module 40, the ultrasonic wave received due to the plane wave reflecting on the outer surface of the cortical bone 10 may be referred to as the outer-surface reflection wave, and similarly the ultrasonic wave received due to the plane wave reflecting on the inner surface of the cortical bone 10 may be referred to as the inner-surface reflection wave. Moreover, when the oscillator pairs 25 need to be differentiated from each other, a large-letter alphabet is sequentially added to the end of each reference numeral from the side of the oscillator 24a at the end of the array, so that they are expressed as the oscillator pair 25A, the oscillator pair 25B, and so on.

Figure 6A:
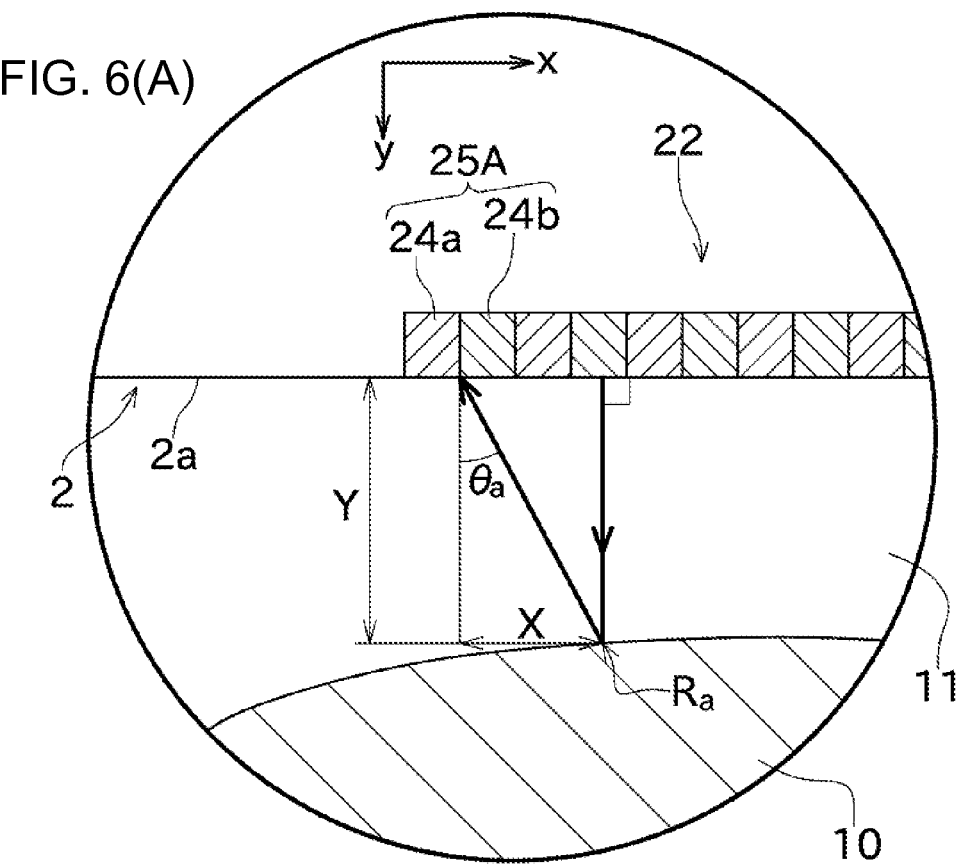
FIG. 6(A) is a schematic view illustrating, in an enlarged manner, an area around an oscillator pair receiving an outer-surface reflection wave.
Figure 6B:
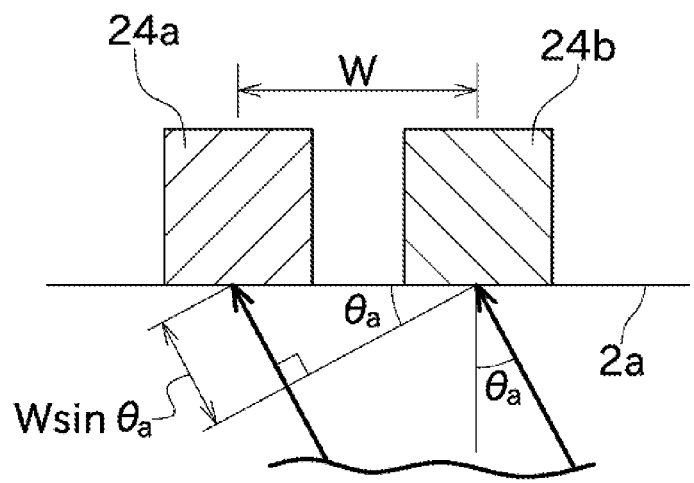
FIG. 6(B) is a schematic view for describing a difference in propagation paths of outer-surface reflection waves arriving at two oscillators configuring the oscillator pair.

Hereinafter, the detection of the arrival directions is specifically described with reference to FIGS. 6(A)-6(B). FIG. 6(A) is a schematic view illustrating, in an enlarged manner, an area around the oscillator pair 25A receiving an outer-surface reflection wave, and FIG. 6(B) is a schematic view for describing a difference in propagation paths of outer-surface reflection waves arriving at the two oscillators 24a and 24b configuring the corresponding oscillator pair. In a certain oscillator pair 25, the arrival directions of the outer-surface reflection waves with respect to the adjacent two oscillators 24 are similar. For example, in FIGS. 6(A)-6(B), it can be assumed that the outer-surface reflection waves arrive at an arrival angle $\theta_a$ at the respective oscillators 24a and 24b configuring the oscillator pair 25A. Here, the following operation is performed to obtain the arrival angle $\theta_a$.

First, the arrival direction detecting submodule 41 measures a time difference $\Delta t$ when the two oscillators 24a and 24b configuring the oscillator pair 25A detect the peaks of the outer-surface reflection waves. Note that, although the outer-surface and inner-surface reflection waves are produced by transmitting the plane wave from the array oscillator set 22 as described above, since the outer-surface reflection waves are always received earlier than the inner-surface reflection waves, the peaks of the outer-surface reflection waves can suitably be detected.

Subsequently, the arrival angle $\theta_a$ of the outer-surface reflection waves with respect to the oscillator pair 25A is obtained based on the time difference $\Delta t$. As illustrated in FIG. 6(B), when an interval between the oscillator 24a and the oscillator 24b is W, the outer-surface reflection wave which arrives at the oscillator 24a propagates a distance longer by $W \sin \theta_a$ compared to propagating to the oscillator 24b. Here, when the speed of sound inside the soft tissue is $SOS_{soft}$, $SOS_{soft} \Delta t = W \sin \theta_a$. Therefore, the arrival angle $\theta_a$ can be obtained based on $\theta_a = \arcsin(SOS_{soft} \Delta t/W)$. The arrival direction detecting submodule 41 similarly obtains the arrival angles for the other oscillator pairs 25. Note that, although the value obtained from experience is used as the speed of sound $SOS_{soft}$ inside the soft tissue 11 in this embodiment, an actual measurement value may be used.

Next, the arrival time length detecting submodule 42 is described. The arrival time length detecting submodule 42 obtains an arrival time length $T_a$ from the transmission of the ultrasonic waves by the array oscillator set 22 until the arrival of the outer-surface reflection waves at the oscillator pair 25. In this embodiment, an average value of the time lengths from the transmission of the ultrasonic waves by the array oscillator set 22 until the outer-surface reflection waves arrive at the respective two oscillators 24 configuring the oscillator pair 25 is obtained as the arrival time length $T_a$. Note that, without limiting to the average value, for example, the time length for the outer-surface reflection wave to arrive at one of the oscillators 24 may be used as the arrival time length $T_a$ as it is.

Next, the outer-surface reflection point detecting submodule 43 is described. The outer-surface reflection point detecting submodule 43 detects a reflection point $R_a$ of each of the outer-surface reflection waves arrived at each oscillator pair 25 based on the arrival angle $\theta_a$ and the arrival time length $T_a$.

Here, in the plane face illustrated in FIGS. 6(A)-6(B), the direction in which the array oscillator set 22 is aligned is the X-axis and the direction orthogonal to the X-axis is the Y-axis. Further, a distance from the oscillator pair 25A to the reflection point R. in the X-axis direction is X and the distance thereof in the Y-axis direction is Y. As it is clear from FIGS. 6(A)-6(B), a propagation distance $L_a$ of the outer-surface reflection waves is $L_a = Y + Y/\cos \theta_a$. On the other hand, when using the arrival time length $T_a$ and the speed of sound $SOS_{soft}$ inside the soft tissue 11, $L_a = SOS_{soft} \times T_a$; thus, the distances X and Y indicating the position of the reflection point $R_a$ can be obtained based on $Y = SOS_{soft} \times T_a \times \cos \theta/(1+\cos \theta)$ and $X = Y \times \tan \theta = SOS_{soft} \times T_a \times \sin \theta/(1+\cos \theta)$. As above, the position of the reflection point $R^a$ can be calculated based on the arrival angle $\theta_a$ and the arrival time length $T_a$ of the plane wave. Further, the outer-surface reflection point detecting submodule 43 similarly obtains the reflection points for the other oscillator pairs 25.

The bone outer-surface line detecting submodule 44 detects a bone outer-surface line by coupling, with either one of a straight line and a curve line, the plurality of reflection points obtained by the outer-surface reflection point detecting submodule 43. Since the reflection points are on the outer surface of the cortical bone 10, the bone outer-surface line indicates the outer surface shape of the cortical bone 10.

In the above manner, the outer surface shape (bone outer-surface line) of the cortical bone 10 can be obtained by the shape detecting module 40.

Next, the reception waveform storage 50 is described. The reception waveform storage 50 repeats processing of transmitting the ultrasonic wave from one of the plurality of oscillators 24 to the cortical bone 10 and storing each of the reception waveforms (waveform signals) of all the oscillators 24, while changing the transmission-side oscillator 24 one by one.

Therefore, when the number of the oscillators 24 configuring the array oscillator set 22 is N, there are N×N kinds of reception waveforms to be stored. Note that, in the following description, the reception waveform when the transmission-side oscillator 24 is the i-th oscillator and the reception-side oscillator 24 is the j-th oscillator may be expressed as $s_{ij}(t)$.

Note that, the function of the reception waveform storage 50 corresponds to the processing at S102 to S104 (reception waveform storing process) in the flowchart of FIG. 4. Hereinafter, to explain along the flowchart, the operator 35 functioning as the reception waveform storage 50 first selects one of the plurality of oscillators 24 configuring the array oscillator set 22 and controls this oscillator 24 to transmit the ultrasonic wave to the cortical bone 10 (S102). Then, the operator 35 receives, by each of the oscillators 24, the ultrasonic wave transmitted from the selected oscillator 24, and acquires the obtained reception waveforms, and stores them in a suitable storing unit, such as a memory (S103). By performing the above processing for all the oscillators 24 (S102 to S104), the reception waveforms of all the oscillators 24 can be acquired and stored for every transmission-side oscillator 24.

Next, the echo waveform synthesizing module 51 is described. The echo waveform synthesizing module 51 moves the focusing position within the cortical bone 10 while forming focusing beams corresponding to each focusing position, and synthesizes an echo waveform. Further, the echo waveform synthesizing module 51 evaluates the echo waveform in view of whether the inner surface of the cortical bone 10 is suitably focused, and selects (acquires) a suitable echo waveform.

Note that, the function of the echo waveform synthesizing module 51 corresponds to the processing at S105 to S109 (echo waveform synthesizing process) in the flowchart of FIG. 4. To explain along the flowchart, the operator 35 functioning as the echo waveform synthesizing module 51 first determines the focusing position within the cortical bone 10 (S105). Here, a virtual grid is determined as the dashed lines in FIG. 7(A) by taking the outer-surface shape line of the cortical bone 10 into consideration, and a single point suitably selected from an intersection point group in the virtual grid is used as the focusing position. Next, the operator 35, upon hypothetically determining the speeds of sound inside the cortical bone and the soft tissue, performs simulation of a sound source, and calculates the propagation path from the transmission-side oscillator 24 to the focusing position and further back to the reception-side oscillator 24 (S106). Here, the operator 35 accurately calculates refraction of the path at the bone outer surface based on the known Snell's law by using the bone outer-surface information obtained in the shape detection at S101.

Note that, the reason for the hypothetical determination of the speeds of sound is as follows. That is, regarding the speed of sound $SOS_{soft}$ inside the soft tissue, the variation thereof is within a comparatively small range between 1,450 and 1,585 m/s inside any one of fat, blood and muscle, and therefore, even if the calculation is performed by setting the speed of sound $SOS_{soft}$ to a suitable value within the above range, influence thereof can be considered small. Moreover, regarding the speed of sound $SOS_{bone}$ inside the cortical bone 10, it varies within a range between 2,900 and 3,400 m/s and influence of the variation in the speed of sound on the propagation time length is about slightly less than 20%, whereas, it is known from experience that the thickness of a cortical bone of a tibia of a human body may take a value within a range between 1 and 4 mm. Therefore, the propagation time length of the ultrasonic wave inside the cortical bone 10 greatly receives the influence of the thickness of the cortical bone 10, whereas it does not receive much influence caused by the variation in the speed of sound inside the cortical bone 10. Thus, it can be considered that there is no problem in performing the calculation by setting the speed of sound $SOS_{bone}$ inside the cortical bone 10 to a suitable value within the range between 2,900 and 3,400 m/s. By the above considerations, in this embodiment, the calculation is performed by hypothetically determining (fixing) the speed of sound $SOS_{soft}$ inside the soft tissue and the speed of sound $SOS_{bone}$ inside the cortical bone 10 to be values which can be determined as substantially valid in view of the ease of the calculation and the shortening of the processing time, etc.

Note that, it is needless to say that the refraction and the like of the propagation path of the ultrasonic wave at the bone outer surface may be calculated by using speeds of sound obtained through inputting or measuring, with a suitable method, the speed of sound $SOS_{soft}$ inside the soft tissue and the speed of sound $SOS_{bone}$ inside the cortical bone 10.

To describe the processing at S106 in detail, with the assumption of using the speeds of sound hypothetically determined as above, the operator 35 calculates, through simulation, the propagation path of the ultrasonic wave propagated through the focusing position in the case where the transmission-side oscillator 24 is the i-th oscillator and the reception-side oscillator 24 is the j-th oscillator. The operator 35 calculates a propagation time length $t_{ij}$ based on the calculation result. The propagation time length $t_{ij}$ is calculated while various changing the transmission-side and reception-side oscillators 24.

Next, the operator 35 obtains the shortest $\min(t_{ij})$ among the plurality of obtained propagation time lengths $t_{ij}$, and by subtracting the obtained shortest time length $\min(t_{ij})$ from each propagation time length $t_{ij}$, obtains a delay time length $\Delta t_{ij}$. Specifically, each delay time length $\Delta t_{ij}$ becomes $\Delta t_{ij} = t_{ij} - \min(t_{ij})$.

Next, by using the delay time lengths $\Delta t_{ij}$ obtained above, the operator 35 adds the reception waveforms $s_{ij}(t)$ while shifting them, so as to synthesize an echo waveform $s(t)$ corresponding to the focusing beams (opening synthesis by post processing, S107). Specifically, the echo waveform $s(t)$ can be obtained based on $s(t) = \Sigma s_{ij}(t - \Delta t_{ij})$.

Then, the operator 35 performs known enveloping processing on the obtained echo waveform $s(t)$ and forms an echo pattern $S(t)$ (S108).

Figure 8:
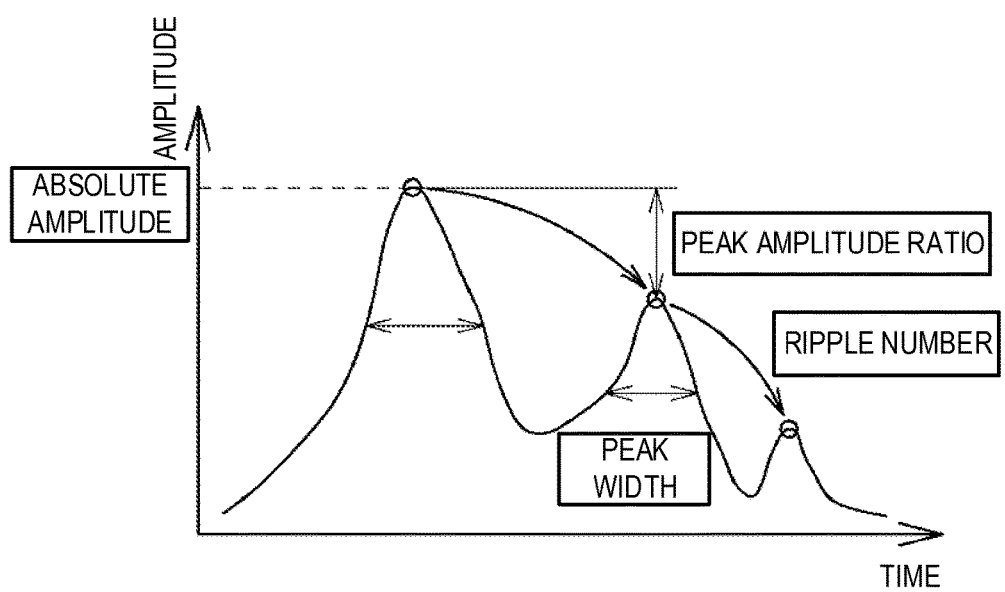
FIG. 8 is a chart exemplarily illustrating indexes for evaluating an envelope waveform.

Next, with the obtained echo pattern $S(t)$, the operator 35 evaluates whether the beams are suitably focused on the inner surface of the cortical bone 10 (S109). Although various methods can be considered for the evaluation, for example, quantitative indexes, such as peak amplitude ratio, a peak width, an absolute amplitude, and a peak ripple number which are illustrated in FIG. 8, may be used singly or in combination.

Here, the peak amplitude ratio is the ratio of reduction of a second peak in the appearing order, compared to a first peak in the appearing order. The peak width is the width of the peak at a height obtained from multiplying the total height of the peak by a predetermined ratio (e.g., 0.7). The absolute amplitude is the total height of the first peak in the appearing order. The peak ripple number is the number obtained by counting the pulsation (concaves and convexes) appearing in the echo pattern.

Note that, in the evaluation performed at S109, for example, a method such as the inner-surface reflection wave is determined to be suitably separated if the peak ripple number is two or three and the absolute amplitudes of the first peak (outer surface echo) and the second peak (inner surface echo) are higher than respective predetermined thresholds can be used. In other words, the index(es) that can discriminate a waveform in which the phases of the echoes match at the second peak portion indicating the inner-surface reflection waves and strengthen each other, may be used.

As a result of the evaluation of the echo pattern, if the inner-surface reflection waves of the cortical bone 10 are determined that they suitably appear in the echo pattern, the operator 35 proceeds to the next processing, the thickness calculation. If the inner-surface reflection waves of the cortical bone 10 are determined that they do not suitably appear in the echo pattern, the operator 35 returns to S105 and suitably shifts the focusing position within the plane face orthogonal to the contact face $2a$ and parallel to the direction in which the oscillators 24 are aligned in the array oscillator set 22. Here, among the intersection points of the virtual grid in FIG. 7(A), the focusing position is reset to an intersection point different from the immediately-previously set focusing position. Then, the processing at S106 to S108 described above is repeated.

Figure 7A:
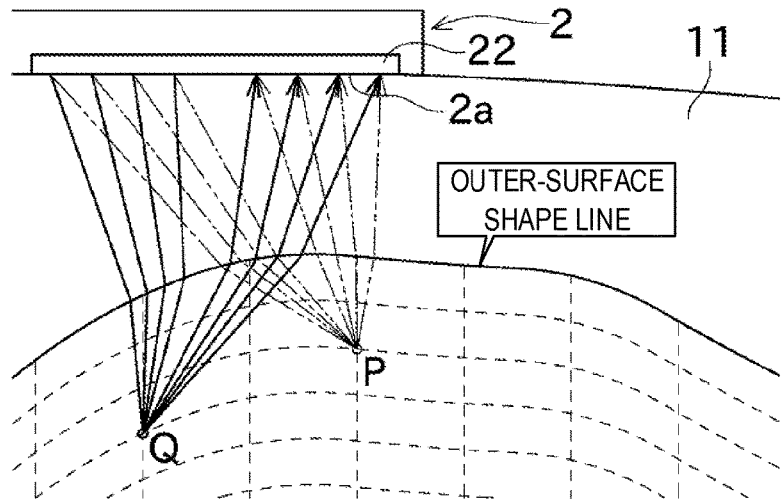
FIG. 7(A) is a conceptual view illustrating a situation where beam forming is performed while changing a focusing position.
Figure 7B:
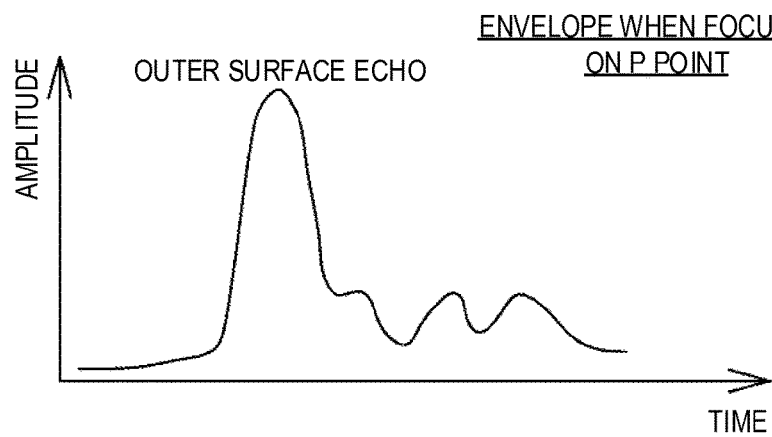
FIG. 7(B) is a chart illustrating an envelope of reception waveforms when the focusing position is at P point.

Thus, the echo waveform synthesizing module 51 creates the echo patterns by sequentially synthesizing the echo waveforms while scanning the focusing positions over the virtual grid in FIG. 7(A) until the inner-surface reflection waves of the cortical bone 10 are determined to suitably appear in the evaluation at S109. Therefore, a single echo pattern is obtained every time the processing at S105 to S108 is performed once (i.e., for every focusing position). In FIG. 7(B), an example of the echo pattern when the focusing position is set to P point in FIG. 7(A) is illustrated, and in FIG. 7(C), an example of the echo pattern when the focusing position is set to Q point in FIG. 7(A) is illustrated. The inner-surface focusing waveform acquiring module 52 evaluates the various echo waveforms obtained as above and discriminates the waveform in which the inner-surface reflection waves suitably appear, such as the waveform in FIG. 7(C). Thus, the echo waveform with the beams suitably focusing on the inner surface of the cortical bone 10 can be found.

Next, the thickness calculating module 53 is described. The thickness calculating module 53 calculates the thickness of the cortical bone 10 based on the echo waveform obtained by the inner-surface focusing waveform acquiring module 52. Note that, the function of the thickness calculating module 53 corresponds to the processing at S110 in the flowchart of FIG. 4 (echo waveform synthesizing process).

Specifically, the operator 35 functions as the thickness calculating module 53. The operator 35 obtains a time difference between the largest peak and the peak appearing next to the largest peak in the echo waveform (echo pattern) described above, and calculates the thickness of the cortical bone 10 based on the equation below.

Figure 7C:
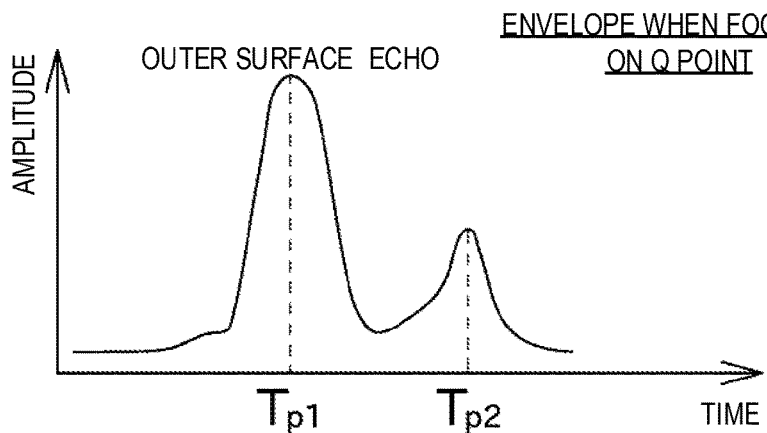
FIG. 7(C) is a chart illustrating an envelope of reception waveforms when the focusing position is at Q point.

That is, when the speed of sound inside the cortical bone is $SOS_{bone}$, the timing at which the largest peak appears in the echo pattern (see FIG. 7(C)) is $T_{p1}$, and the timing at which the next peak appears is $T_{p2}$, a thickness E of the cortical bone 10 can be obtained based on $E = SOS_{bone} \times (T_{p2} - T_{p1})/2$.

The above is the description of the cortical bone thickness measuring device 1 and the thickness measuring method of this embodiment, and in the above manner, the thickness of the cortical bone 10 can accurately be obtained by the interference of cavities $10a$ and the like.

Note that, to verify the result of the actual measurement of the thickness of the cortical bone 10 of the human body performed by the cortical bone thickness measuring device 1 of this embodiment, the present inventor(s) captured a CT section image of the same part of the same examinee and compared the result with the obtained CT image. Then, as a result of comparing the thickness measurement data of the cortical bone 10 with the CT image, it was confirmed that the measurement value matches with the CT image at high accuracy. Therefore, it was proved that the cortical bone thickness measuring device 1 of this embodiment can measure the thickness of the cortical bone 10 at high accuracy.

As described above, the cortical bone thickness measuring device 1 of this embodiment includes the plurality of oscillators 24, the reception waveform storage 50, the echo waveform synthesizing module 51, the inner-surface focusing waveform acquiring module 52, and the thickness calculating module 53. The plurality of oscillators 24 are aligned and each of them is configured to be able to transmit the ultrasonic wave to the cortical bone 10 and acquire the echo signal of the ultrasonic wave. The reception waveform storage 50 acquires and stores the reception waveforms of all the oscillators 24 every time the ultrasonic wave is transmitted from each of the oscillators 24. The echo waveform synthesizing module 51 acquires the echo waveform corresponding to the ultrasonic beams by synthesizing the reception waveforms of the respective oscillators 24 stored in the reception waveform storage 50, while scanning the focusing position of the ultrasonic beams. The inner-surface focusing waveform acquiring module 52 acquires the echo waveform with the beams suitably focusing on the inner surface of the cortical bone 10, by evaluating the echo waveform obtained by the echo waveform synthesizing module 51. The thickness calculating module 53 calculates the thickness of the cortical bone 10 based on the echo waveform acquired by the inner-surface focusing waveform acquiring module 52.

Thus, even in an environment where many cavities exist between the outer surface and the inner surface or many unnecessary echoes are obtained, the thickness of the cortical bone 10 can be measured at suitable accuracy.

Although the suitable embodiment of this disclosure is described above, the above configurations may be modified as follows.

The scanning of the focusing position may be cancelled when the value of the evaluation quantitative index(s) indicating whether the beams are focused on the inner surface of the cortical bone 10 becomes higher than a predetermined threshold; however, upon scanning all the positions, the focusing waveform in which the value of the evaluation index(s) indicates a highest value may be selected.

The focusing position is not limited to be scanned two-dimensionally along the virtual grid on the outer-surface shape line of the cortical bone 10 as illustrated in FIG. 7(A), and it may be scanned two-dimensionally in the direction parallel to the longitudinal direction of the array oscillator set 22 (direction in which the oscillators 24 are aligned) and the direction orthogonal to the contact face 2a. Moreover, the focusing position may be scanned single-dimensionally only in the direction orthogonal to the contact face 2a.

The echo waveform obtained by the synthesis may be configured such that whether the inner surface is suitably focused is evaluated without being enveloped.

The operator 35 described above may be modified to be provided to the ultrasonic wave transducer 2 side. Moreover, without limited to the configuration in which the ultrasonic wave transducer 2 and the device body 3 are provided separately, the ultrasonic wave transducer 2 and the device body 3 may be integrated.

The application of the thickness measuring device of this disclosure is not limited to measuring thicknesses of bones, and it may be broadly applied to other applications. For example, it can be considered to use the thickness measuring device in non-destructive examinations including measuring the thickness of a metal pipe with the possibility of internal corrosion, etc.

DESCRIPTION OF REFERENCE NUMERAL(S)

1 Cortical Bone Thickness Measuring Device (Thickness Measuring Device)
24 Oscillator (Transducing Part)
40 Shape Detecting Module
50 Reception Waveform Storage
51 Echo Waveform Synthesizing Module
52 Inner-surface Focusing Waveform Acquiring Module
53 Thickness Calculating Module

What is claimed is:
1. A thickness measuring device, comprising:
a plurality of elements arranged in line, each of the elements being configured to transmit an ultrasonic wave to a target object and acquirable of an echo signal with respect to the ultrasonic wave;
a reception waveform storage configured to acquire and store reception waveforms of the elements at the time the respective elements transmit the ultrasonic waves;
an echo waveform synthesizing module configured to obtain echo waveforms corresponding to the ultrasonic wave while scanning a focusing position of the ultrasonic beams, each of the echo waveforms being obtained by synthesizing the reception waveforms of the respective element stored in the reception waveform storage;
an inner-surface focusing waveform acquiring module configured to acquire the echo waveform in which the beams are suitably focused on an inner surface of the target object, by evaluating each of the echo waveforms obtained by the echo waveform synthesizing module; and
a thickness calculating module configured to calculate a thickness of the target object based on the echo waveform acquired by the inner-surface focusing waveform acquiring module.

2. The thickness measuring device of claim 1, comprising an outer-surface detecting module configured to detect a position and shape of an outer surface of the target object, wherein the echo waveform synthesizing module, upon acquiring or hypothetically determining speeds of sound inside and outside the target object, calculates a path of the ultrasonic wave arriving at the elements used on the reception side from the elements used on the transmission side via the focusing position by taking into consideration refraction of the path at the outer surface of the target object acquired by the outer-surface detecting module, and the echo waveform synthesizing module acquires the echo waveforms by synthesizing the reception waveforms based on the calculation result while scanning the focusing position.

3. The thickness measuring device of claim 2, wherein the echo waveform synthesizing module calculates a propagation time length of the ultrasonic wave arriving at the elements used on the reception side from the elements used on the transmission side via the focusing position, and the echo waveform synthesizing module acquires the echo waveforms by synthesizing the reception waveforms while scanning the focusing position, each of the reception waveforms being synthesized while being shifted by a delay time length calculated based on the propagation time length.

4. The thickness measuring device of claim 3, wherein the echo waveform synthesizing module scans the focusing position of the ultrasonic beams two-dimensionally.

5. The thickness measuring device of claim 3, wherein the inner-surface focusing waveform acquiring module acquires the echo waveform in which the beams are suitably focused on the inner surface of the target object, by forming each of the synthesized echo waveforms into an envelope and evaluates a shape of an echo pattern obtained from the envelope.

6. The thickness measuring device of claim 3, wherein the thickness calculating module calculates the thickness of the target object based on a time difference between an outer surface echo and an inner surface echo that appear in the echo waveform acquired by the inner surface focusing waveform acquiring module.

7. The thickness measuring device of claim 2, wherein the echo waveform synthesizing module scans the focusing position of the ultrasonic beams two-dimensionally.

8. The thickness measuring device of claim 7, wherein the thickness calculating module calculates the thickness of the target object based on a time difference between an outer surface echo and an inner surface echo that appear in the echo waveform acquired by the inner surface focusing waveform acquiring module.

9. The thickness measuring device of claim 2, wherein the inner-surface focusing waveform acquiring module acquires the echo waveform in which the beams are suitably focused on the inner surface of the target object, by forming each of the synthesized echo waveforms into an envelope and evaluates a shape of an echo pattern obtained from the envelope.

10. The thickness measuring device of claim 2, wherein the thickness calculating module calculates the thickness of the target object based on a time difference between an outer surface echo and an inner surface echo that appear in the echo waveform acquired by the inner surface focusing waveform acquiring module.

11. The thickness measuring device of claim 2, wherein the target object is a cortical bone.

12. The thickness measuring device of claim 1, wherein the echo waveform synthesizing module scans the focusing position of the ultrasonic beams two-dimensionally.

13. The thickness measuring device of claim 12, wherein the inner-surface focusing waveform acquiring module acquires the echo waveform in which the beams are suitably focused on the inner surface of the target object, by forming each of the synthesized echo waveforms into an envelope and evaluates a shape of an echo pattern obtained from the envelope.

14. The thickness measuring device of claim 12, wherein the thickness calculating module calculates the thickness of the target object based on a time difference between an outer surface echo and an inner surface echo that appear in the echo waveform acquired by the inner surface focusing waveform acquiring module.

15. The thickness measuring device of claim 1, wherein the inner-surface focusing waveform acquiring module acquires the echo waveform in which the beams are suitably focused on the inner surface of the target object, by forming each of the synthesized echo waveforms into an envelope and evaluates a shape of an echo pattern obtained from the envelope.

16. The thickness measuring device of claim 1, wherein the thickness calculating module calculates the thickness of the target object based on a time difference between an outer surface echo and an inner surface echo that appear in the echo waveform acquired by the inner surface focusing waveform acquiring module.

17. The thickness measuring device of claim 1, comprising an array oscillator set provided with oscillators arranged in line, the oscillators being the plurality of elements.

18. The thickness measuring device of claim 17, wherein the plurality of oscillators provided in the array oscillator set are transmittable of ultrasonic waves simultaneously and also transmittable of the ultrasonic waves at individual timings.

19. The thickness measuring device of claim 1, wherein the target object is a cortical bone.

20. A method of measuring a thickness by a thickness measuring device including a plurality of elements arranged in line, each of the elements being configured to transmit an ultrasonic wave to a target object and acquire an echo signal with respect to the ultrasonic wave, the method comprising:

acquiring and storing reception waveforms of all of the elements every time each elements transmits the ultrasonic wave;

obtaining echo waveforms corresponding to the ultrasonic wave while scanning a focusing position of the ultrasonic beams, each of the echo waveforms being obtained by synthesizing the reception waveforms of the respective elements stored by the acquiring and storing the reception waveforms;

acquiring the echo waveform in which the beams are suitably focused on an inner surface of the target object, by evaluating each of the echo waveforms obtained by the obtaining the echo waveforms; and calculating a thickness of the target object based on the echo waveform acquired by the acquiring the echo waveform.

* * * * *